(12) United States Patent
Shobayashi et al.

(10) Patent No.: US 11,877,939 B2
(45) Date of Patent: Jan. 23, 2024

(54) STENT AND CATHETER-STENT SYSTEM

(71) Applicant: Biomedical Solutions Inc., Tokyo (JP)

(72) Inventors: Yasuhiro Shobayashi, Tokyo (JP); Atsunori Yoshida, Tokyo (JP)

(73) Assignee: OTSUKA MEDICAL DEVICES CO., LTD., Tokyo (JP)

( * ) Notice: Subject to any disclaimer, the term of this patent is extended or adjusted under 35 U.S.C. 154(b) by 482 days.

(21) Appl. No.: 17/211,169

(22) Filed: Mar. 24, 2021

(65) Prior Publication Data
US 2021/0298926 A1 Sep. 30, 2021

(30) Foreign Application Priority Data

Mar. 31, 2020 (JP) .................................. 2020-063410

(51) Int. Cl.
*A61F 2/76* (2006.01)
*A61B 17/22* (2006.01)
*A61F 2/88* (2006.01)

(52) U.S. Cl.
CPC .......... *A61F 2/76* (2013.01); *A61B 17/22031* (2013.01); *A61F 2/885* (2013.01);
(Continued)

(58) Field of Classification Search
CPC .... A61F 2/76; A61F 2/885; A61F 2002/7635; A61F 2230/0091; A61F 2240/008;
(Continued)

(56) References Cited

U.S. PATENT DOCUMENTS 7,632,303 B1 * 12/2009 Stalker ...................... A61F 2/95
623/1.2
2001/0025195 A1 * 9/2001 Shaolian .................. A61F 2/856
623/1.13
(Continued)

FOREIGN PATENT DOCUMENTS

CN 207768466 U 8/2018
EP 2939640 A1 11/2015
(Continued)

OTHER PUBLICATIONS

Extended European Search Report dated Sep. 23, 2021 in EP Application No. 21164248.3, 7 pages.

*Primary Examiner* — Francis C Gray
(74) *Attorney, Agent, or Firm* — Muncy, Geissler, Olds & Lowe, P.C.

(57) ABSTRACT

The stent has an expansive force 0.05 N/mm or less per unit length when it has a diameter equal to the lower limit diameter of the target blood vessel and is measured under the following conditions. A radial force testing system manufactured by Blockwise Engineering LLC is used as a tester. The test conditions include a temperature of 37° C.±2° C. in the chamber of the tester; a stent diameter of 0.5 mm for start of test, and a rate of increase of diameter of 0.5 mm/s in the tester. The test method includes radially compressing the stent disposed in the chamber; recording an expansive force while gradually increasing the diameter of the chamber at the rate of increase of diameter; and dividing the expansive force by the effective length of the stent to calculate an expansive force per unit length.

6 Claims, 15 Drawing Sheets

(52) U.S. Cl.
CPC .......... *A61F 2002/7635* (2013.01); *A61F 2230/0091* (2013.01); *A61F 2240/008* (2013.01); *A61F 2250/001* (2013.01)

(58) Field of Classification Search
CPC ........ A61F 2250/001; A61F 2/89; A61F 2/91; A61F 2/97; A61B 2017/22034; A61B 2017/2215; A61B 17/221; A61B 17/22; A61B 2017/22045
See application file for complete search history.

(56) References Cited

U.S. PATENT DOCUMENTS

| | | | |
|---|---|---|---|
| 2016/0101221 A1* | 4/2016 | Flomenblit | A61F 2/844 623/1.18 |
| 2018/0221181 A1* | 8/2018 | Fischer | A61F 2/915 |
| 2019/0000492 A1 | 1/2019 | Casey et al. | |
| 2019/0201218 A1 | 7/2019 | Shobayashi | |
| 2020/0138612 A1* | 5/2020 | Higashi | A61F 2/915 |
| 2020/0405920 A1 | 12/2020 | Matsushita et al. | |

FOREIGN PATENT DOCUMENTS

| | | | | |
|---|---|---|---|---|
| JP | H08196642 A | 8/1996 | | |
| JP | 2017-506941 A | 3/2017 | | |
| JP | 2019-5587 A | 1/2019 | | |
| JP | 2019-069290 A | 5/2019 | | |
| KR | 2020-0024429 A | 3/2020 | | |
| WO | WO-2015/116690 A1 | 8/2015 | | |
| WO | WO-2019009433 A1 * | 1/2019 | ............ | A61F 2/915 |
| WO | WO2019064306 A1 | 4/2019 | | |
| WO | WO2019176345 A1 | 9/2019 | | |

* cited by examiner

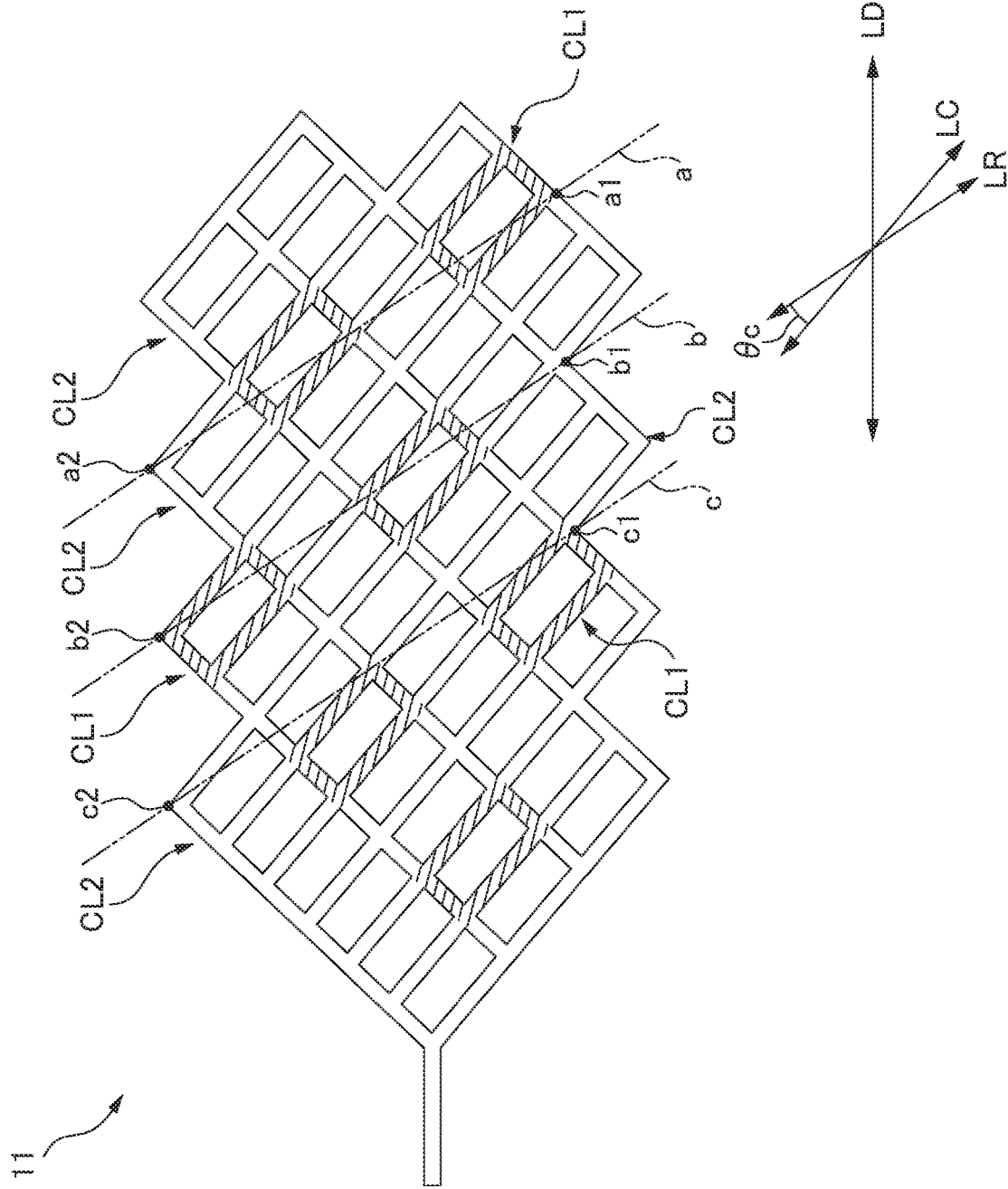

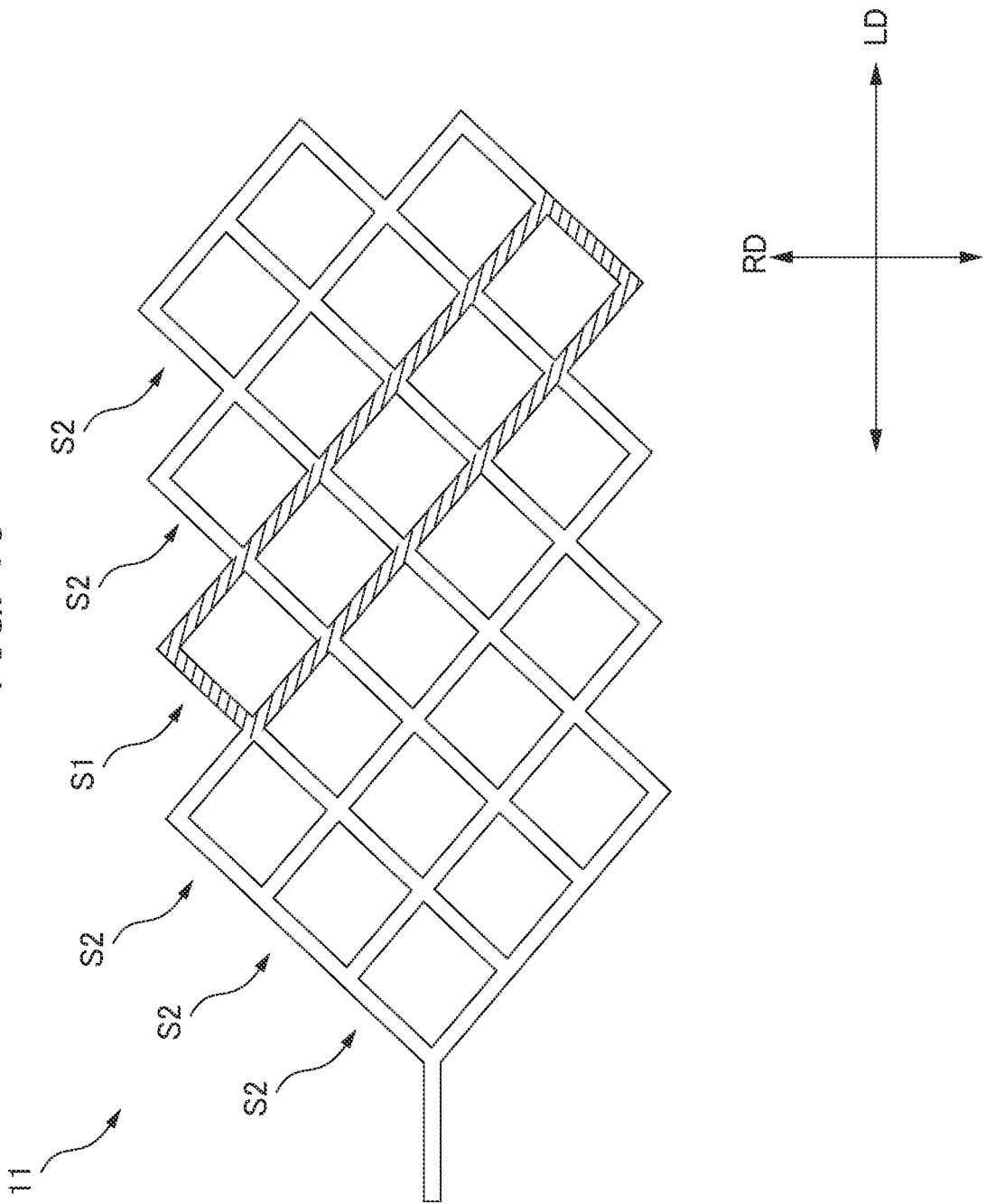

STENT AND CATHETER-STENT SYSTEM

This application is based on and claims the benefit of priority from Japanese Patent Application 2020-063410, filed on 31 Mar. 2020, the content of which is incorporated herein by reference.

BACKGROUND OF THE INVENTION

Field of the Invention

The present invention relates to a stent and a catheter-stent system including the stent.

Related Art

A conventional retrieval stent system used to retrieve a formed blood clot from a blood vessel includes a wire and a stent attached to the distal end of the wire. When such a stent system is used, the stent is inserted into a blood vessel to capture a blood clot, and then the wire is pulled through the catheter so that the blood clot-capturing stent attached to the wire is pulled out of the body to retrieve the blood clot (see, for example, Patent Document 1).

Patent Document 1: Japanese Unexamined Patent Application, Publication No. 2019-005587

SUMMARY OF THE INVENTION

Another stent is also proposed, which is configured to be pushed out of a catheter and configured to deploy while rotating and swinging when it is pushed out of the catheter. Such a stent needs to have an improved ability to capture a blood clot and needs to provide a higher blood clot retrieval rate.

It is an object of the present invention to provide a stent and a catheter-stent system each capable of providing a higher blood clot retrieval rate.

The present invention relates to a stent configured to be inserted into a catheter and to be pushed out of the catheter to capture a blood clot in a blood vessel, the stent including a structure configured to deploy while rotating when a portion of the stent is pushed out of the catheter while another portion of the stent is inserted in the catheter, the stent having an expansive force of 0.05 N/mm or less per unit length when the stent has a diameter equal to a lower limit diameter of a target blood vessel and when the stent is measured using, as a tester, a radial force testing system manufactured by Blockwise Engineering LLC, using test conditions including a temperature of 37° C.±2° C. in a chamber of the tester, a stent diameter of 0.5 mm for start of test, and a rate of increase of diameter of 0.5 mm/s in the tester, and using a test method including:

setting the temperature in the chamber of the tester at 37° C.±2° C.;

placing the whole of the stent in the chamber of the tester and radially contracting the stent until the stent has the diameter for the start of test;

recording an expansive force in a radial direction while gradually increasing the diameter of the chamber at the rate of increase of diameter in the tester; and dividing the expansive force by the effective length of the stent to calculate an expansive force per unit length.

The stent may have a tensile load of 3 N or less as measured using a microcatheter Headway 21 manufactured by MicroVention Inc., a digital force gauge (or push pull gauge), a pulling device, a thermostatic chamber, and a thermometer, using test conditions including a speed of 60 mm/min, a pulling distance equal to the effective length+10 mm, and a test temperature of 37° C.±2° C., and using a test method including:

confirming with the thermometer that the thermostatic chamber has a temperature of 37° C.±2° C.;

placing the microcatheter in the thermostatic chamber;

inserting a stent retriever into the microcatheter from the proximal side until the whole of the stent is housed in the microcatheter;

connecting the proximal end of the stent retriever to the digital force gauge disposed in the pulling device;

fixing the microcatheter with the stent retriever and the microcatheter arranged in a straight line and pulling the stent retriever constantly at the specified speed toward the proximal side using the pulling device; and recording the maximum tensile load measured with the digital force gauge when the stent retriever is pulled over a distance equal to the effective length+10 mm.

The structure in the stent may be configured to deploy while rotating and swinging when a portion of the stent is pushed out of a catheter while another portion of the stent is inserted in the catheter.

The stent may include cells aligned in a direction and may have a rolling direction inclined with respect to the direction in which the cells are aligned. The stent may include a plurality of cells arranged spirally around an axis direction, and the plurality of cells may include at least one cell different in physical property from any other cell.

The stent may include a plurality of crimp pattern portions having a crimp pattern and arranged along an axis direction; and a plurality of coiled elements each provided between adjacent crimp pattern portions of the plurality of crimp pattern portions and extending spirally around an axis, in which each crimp pattern portion may have a top portion, each pair of opposite top portions of the adjacent crimp pattern portions may be connected through each coiled element, each crimp pattern portion may have a cyclic direction inclined with respect to a radial direction perpendicular to the axis direction when viewed in the radial direction, and one of the coiled elements at a one axial end of the crimp pattern portion may have a winding direction the same as or opposite to that of another one of the coiled elements at another axial end of the crimp pattern portion.

The present invention also relates to a catheter-stent system including a catheter and the stent configured to be inserted into the catheter and to be pushed out of the catheter.

The stent and the catheter-stent system according to the present invention provide a higher blood clot retrieval rate.

BRIEF DESCRIPTION OF THE DRAWINGS

FIG. 12 is a developed view of a stent 11 including cells with their physical properties partially modified so that the stent 11 is configured to swing while rotating;

FIG. 13 is a developed view of a stent 11 that includes cells having different line widths so that the stent 11 is configured to rotate;

DETAILED DESCRIPTION OF THE INVENTION

Hereinafter, stents and catheter-stent systems according to embodiments of the present invention will be described with reference to the drawings. First, the entire structure of a stent 11 according to an embodiment of the present invention will be described with reference to FIGS. 1 to 4.

Figure 1:
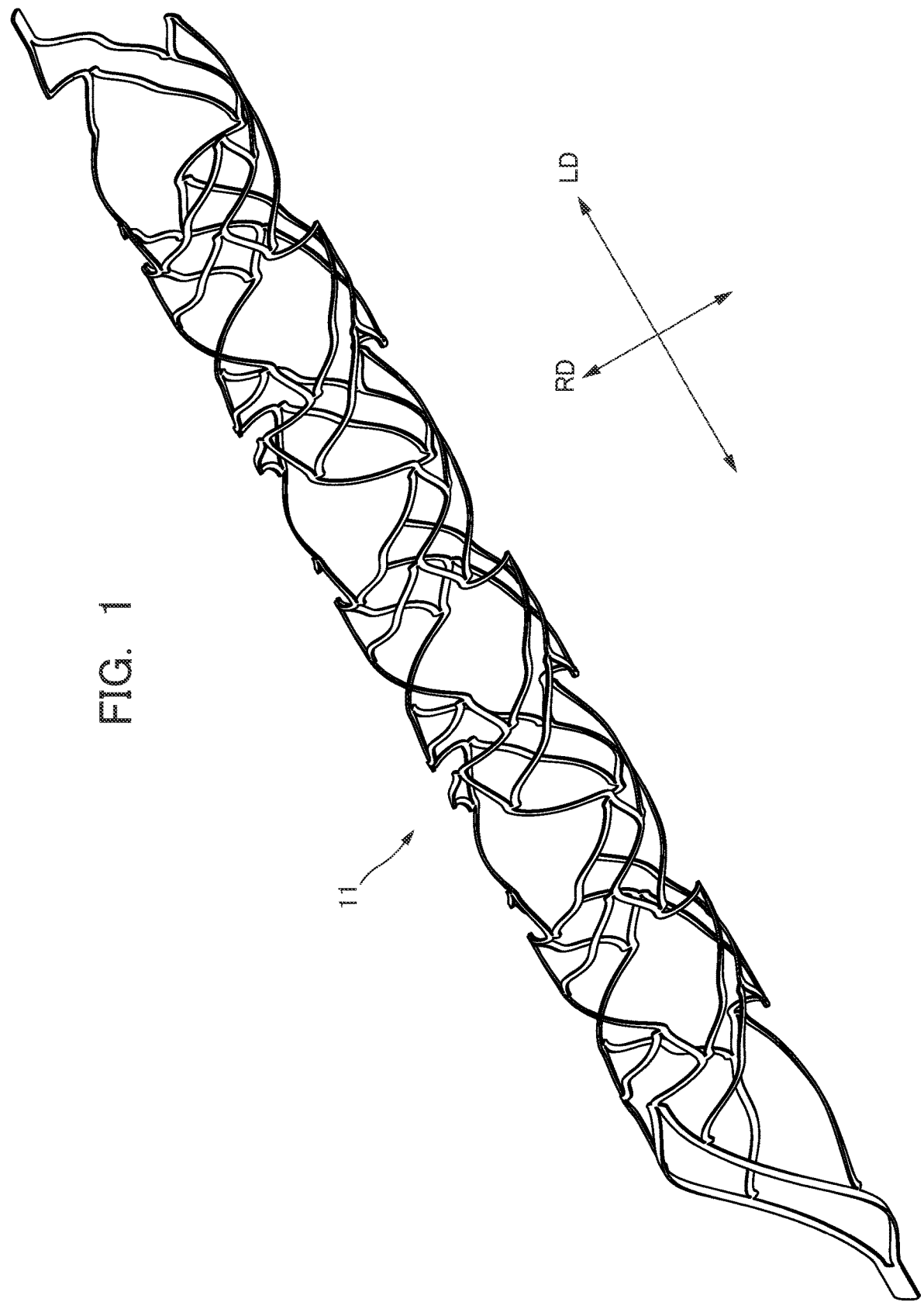
FIG. 1 is a perspective view showing a stent 11 according to an embodiment of the present invention.
Figure 2:
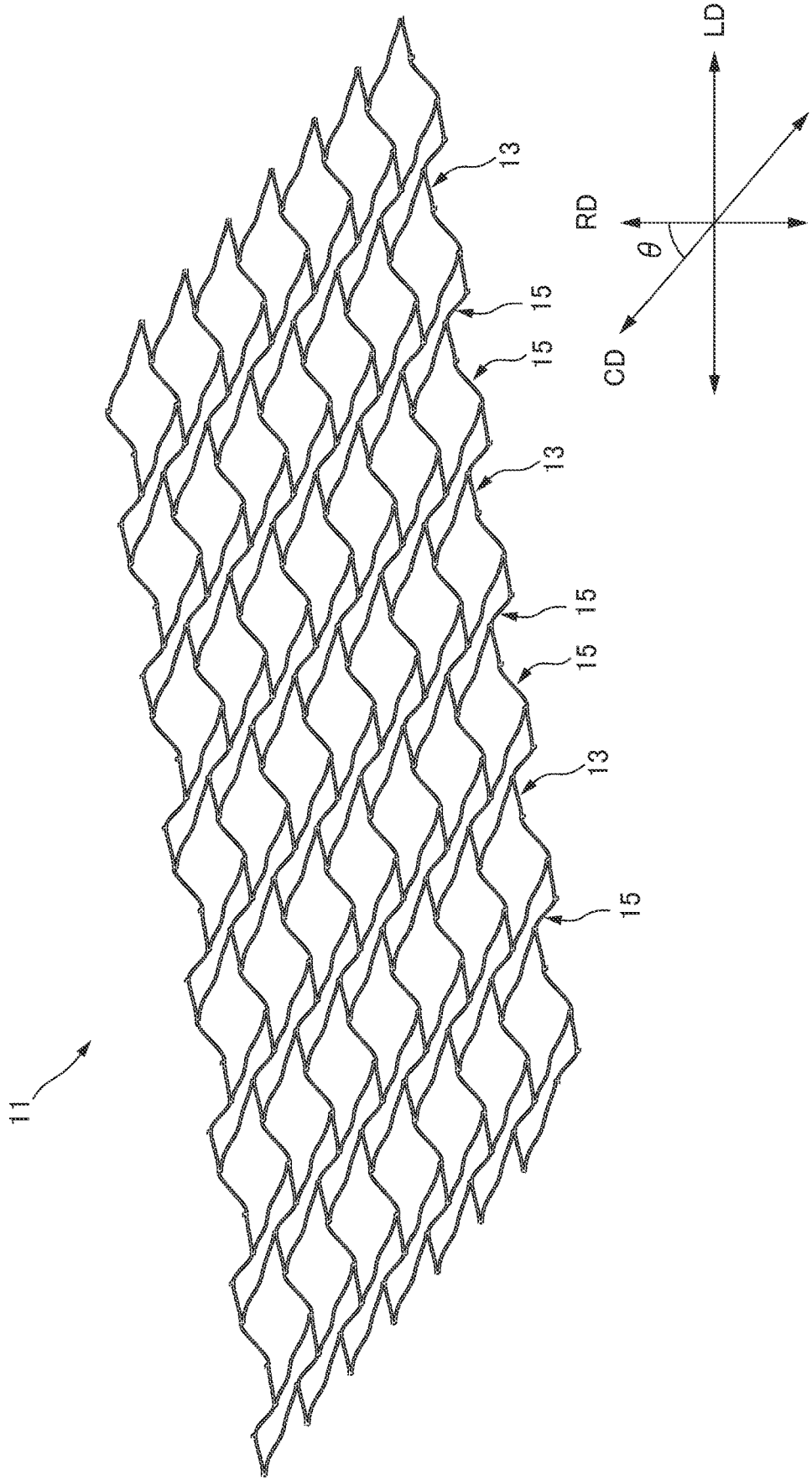
FIG. 2 is a developed view obtained when the stent 11 according to an embodiment is virtually developed in a plane.
Figure 3:
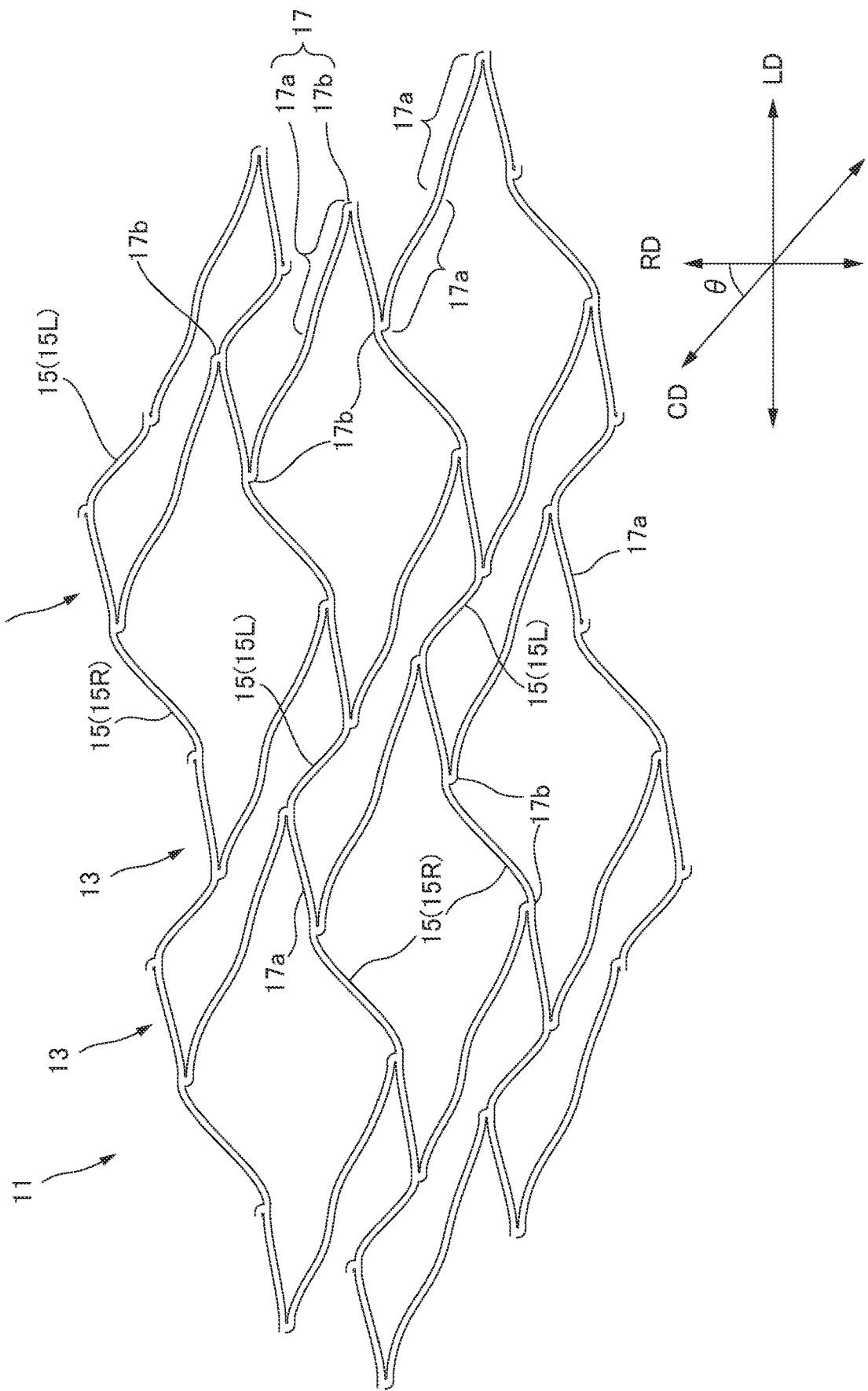
FIG. 3 is a partially enlarged view of the stent 11 shown in FIG. 2.
Figure 4:
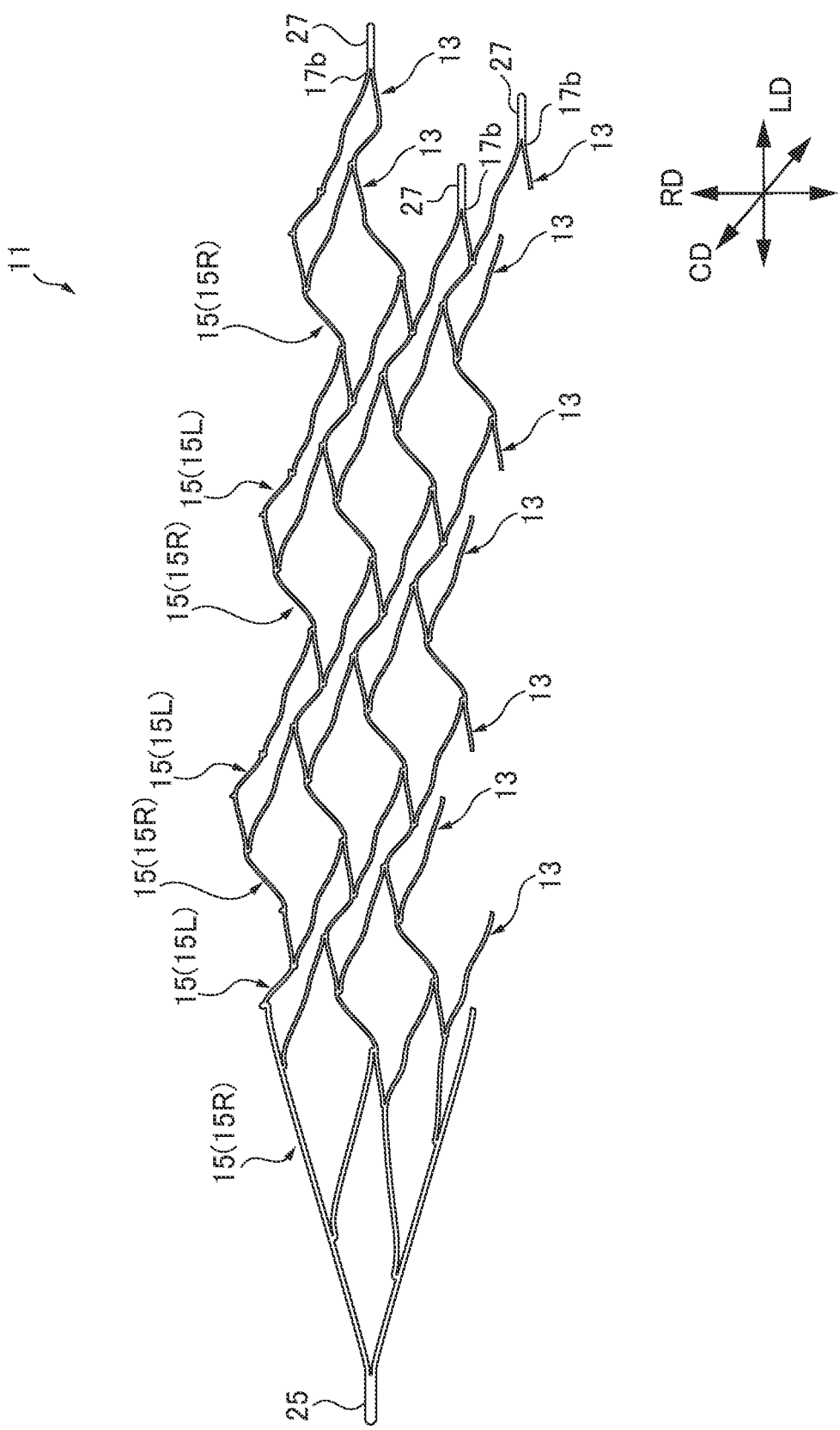
FIG. 4 is a developed view showing the whole of the stent 11 according to an embodiment, which is obtained when the stent 11 is virtually developed in a plane.
Figure 5:
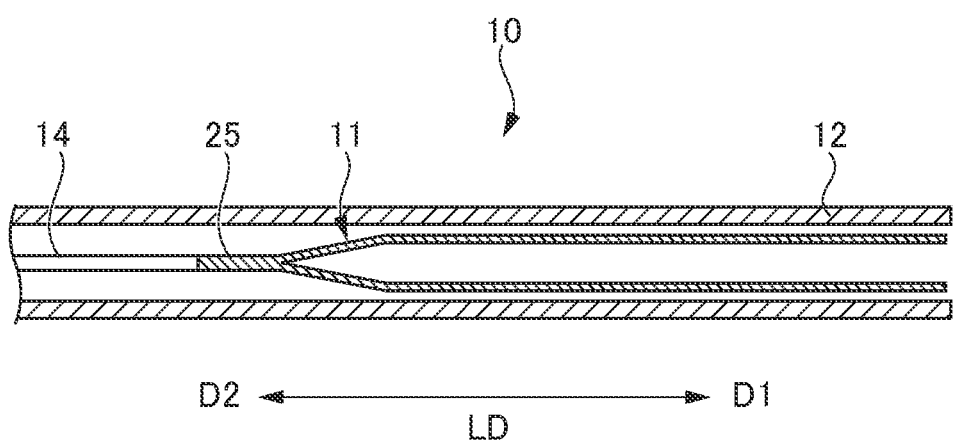
FIG. 5 is a schematic view of a catheter-stent system 10 including the stent 11 according to an embodiment.

FIG. 1 is a perspective view showing the stent 11 according to an embodiment of the present invention. FIG. 2 is a developed view obtained when the stent 11 according to an embodiment is virtually developed in a plane. Both end portions in the axis direction LD of the stent 11 are omitted from FIG. 2. FIG. 3 is a partially enlarged view of the stent 11 shown in FIG. 2. FIG. 4 is a developed view showing the whole of the stent 11 according to an embodiment, which is obtained when the stent 11 is virtually developed in a plane. FIG. 4 shows both end portions in the axis direction LD of the stent 11 in such a way that its full length in the axis direction LD is relatively shortened. FIG. 5 is a schematic view of a catheter-stent system 10 including the stent 11 according to an embodiment. It should be noted that FIGS. 1 to 4 all show the unloaded state of the stent 11. The term "unloaded state" refers to the state of the stent 11 not radially compressed.

As shown in FIG. 1, the stent 11 is substantially cylindrical. The circumferential wall of the stent 11 includes a plurality of closed cells that are congruent in shape and each made of a wire-shaped material surrounding the cell. The stent 11 has a mesh-pattern structure in which the closed cells are closely arranged in the circumferential direction. FIG. 2 is to facilitate the comprehension of the structure of the stent 11, in which the stent 11 is shown in a form developed in a plane. To show the periodicity of the mesh patterns, FIG. 2 virtually illustrates more repeated mesh patterns than those in the actual developed state. As used herein, the term "the circumferential wall of the stent 11" means a portion that separates the inside of the substantially cylindrical structure of the stent 11 from the outside. As used herein, the term "cell" refers to a portion surrounded by a wire-shaped material, which forms the mesh patterns of the stent 11 and is also called an opening or a compartment.

The stent 11 includes rings 13, to form a plurality of crimp patterns, that are arranged side by side in the axis direction LD (namely, the central axis direction); and a plurality of coiled elements 15 each disposed between the rings 13 adjacent to each other in the axis direction LD. As shown in FIG. 3, each ring 13 includes a plurality of substantially V-shaped crimp elements 17 each including two leg portions 17a and a top portion 17b through which the two leg portions 17a are connected, in which the plurality of crimp elements 17 are connected in the cyclic direction CD to form a crimp pattern. Specifically, the substantially V-shaped crimp elements 17 are connected with the top portions 17b disposed on sides opposite to each other.

When the stent 11 is viewed in the radial direction RD perpendicular to the axis direction LD, the cyclic direction CD of the rings 13 is inclined with respect to the radial direction RD. The cyclic direction CD of the rings 13 is inclined at angle θ of, for example, 30 to 60 degrees with respect to the radial direction RD.

Both ends of each coiled element 15 are connected to the opposing top portions 17b of two adjacent rings 13. In this regard, each pair of the opposing top portions 17b of the adjacent rings 13 are connected to each other through each coiled element 15. The stent 11 has what is called a closed cell structure. Specifically, two top portions 17b adjacent to each other along the crimp pattern among three top portions 17b connected through leg portions 17a along the crimp pattern in one of adjacent rings 13 are connected through coiled elements 15 to two top portions 17b adjacent to each other along the crimp pattern among three top portions 17b connected through leg portions 17a along the crimp pattern in the other of the adjacent rings 13 to form a cell. Each top portion 17b of each ring 13 in the crimp pattern is shared by three cells.

The plurality of coiled elements 15 are arranged at equal intervals along the cyclic direction CD of the rings 13. Each coiled element 15 extends spirally around the central axis. As shown in FIG. 3, the winding direction (right-handed) of one (15R) of the coiled elements 15 located on one side with respect to the ring 13 in the axis direction LD is opposite to the winding direction (left-handed) of the other (15L) of the coiled elements 15 located on the other side in the axis direction LD. The length of one coiled element 15R is larger than that of the leg portion 17a but not larger than 1.5 times that of the leg portion 17a. The length of the other coiled element 15L is smaller than that of the leg portion 17a.

As shown in FIG. 4, the stent 11 includes a proximal end portion 25 provided to be connected to a wire (pusher wire) 14 (described later). The proximal end portion 25 is in the form of a single rod, which is to be connected to the wire 14 (described later). The stent 11 also includes three distal end portions 27 provided on a side opposite to the proximal end portion 25. Each distal end portion 27 extends in the axis direction LD from the top portion 17b of the ring 13.

As shown in FIG. 5, the catheter-stent system 10 according to an embodiment of the present invention includes the stent 11 and a catheter 12. While being compressed radially, the stent 11 is inserted in the catheter 12. FIG. 5 schematically shows a cross-section of the radially compressed stent 11. A wire 14 is connected to the proximal end portion 25 of the stent 11. The wire 14 is fed toward the distal side D1 when the stent 11 is pushed to a target site in a blood vessel, and pulled toward the proximal side D2 when the stent 11 is pulled out of the body.

The stent 11 is pushed in by means of the wire 14 to move through the catheter 12 and then pushed out of the distal end of the catheter 12 to deploy at a lesion site. In this process, a pushing device applies a force in the axis direction LD, which is transmitted over the stent 11 while producing an interaction between the ring 13 and the coiled element 15 in the stent 11. Moreover, as will be described later, the stent 11 is configured to deploy while rotating and swinging when the stent 11 is pushed out of the distal end of the catheter 12 while being in an unrestrained state as described later.

Figure 6:
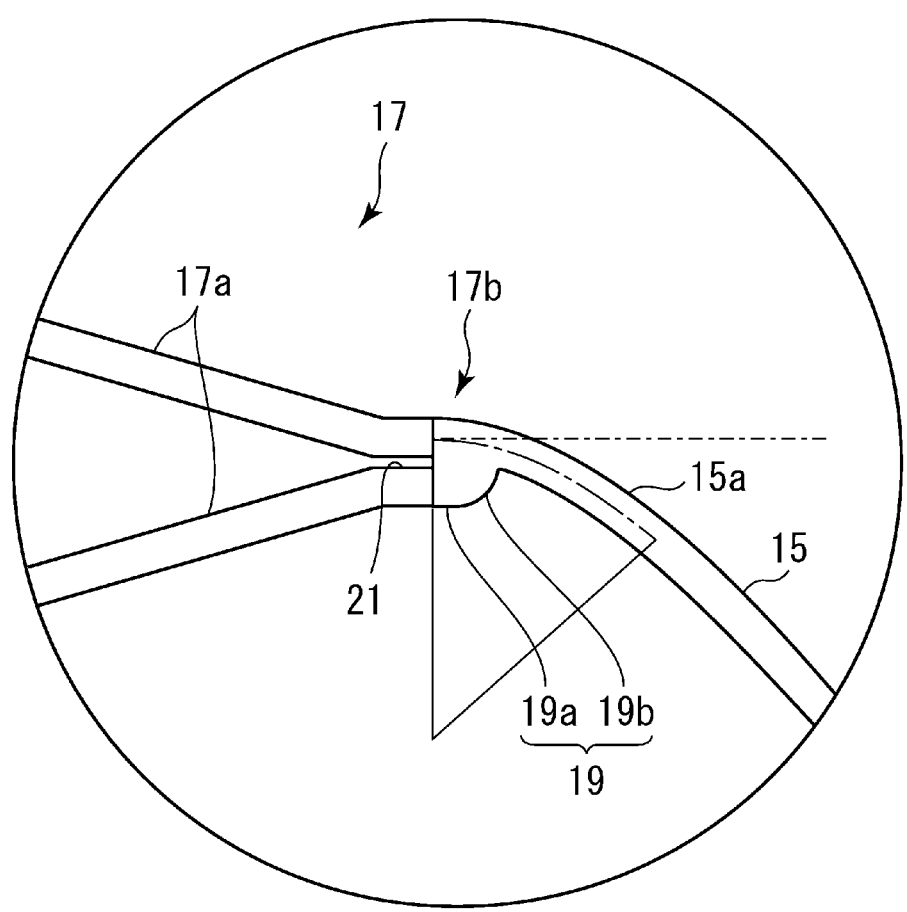
FIG. 6 is a partially enlarged view of the stent 11 shown in FIG. 3.
Figure 7:
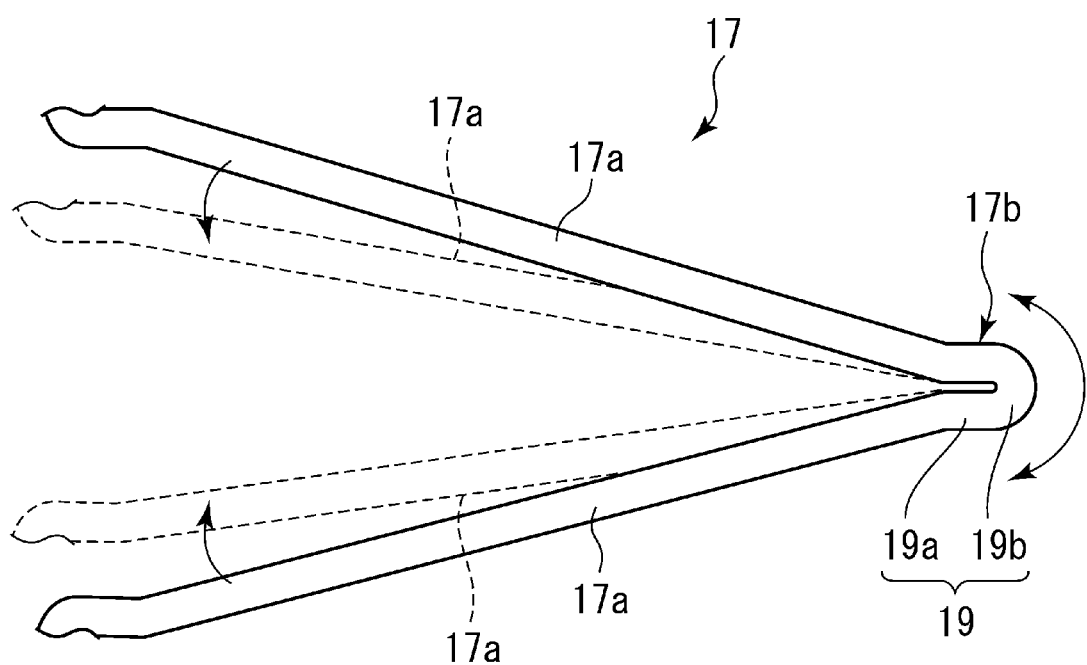
FIG. 7 is an illustrative view showing that a top portion 17b of a crimp element 17 of a ring 13 in the stent 11 can deform when the stent 11 is radially compressed.

Next, the features of the crimp element 17 in the stent 11 will be described in detail. FIG. 6 is a partially enlarged view of the stent 11 shown in FIG. 3. FIG. 7 is an illustrative view showing that the top portion 17b of the crimp element 17 of the ring 13 in the stent 11 can deform when the stent 11 is radially compressed.

As shown in FIGS. 6 and 7, the top portion 17b of the crimp element 17 has a bulge 19. The bulge 19 includes an extension portion 19a extending linearly in the axis direction LD; and a substantially semicircular end portion 19b provided at the top of the extension portion 19a. The extension portion 19a has a width larger than the width of the coiled element 15. The top portion 17b of the crimp element 17 has a slit 21 extending in the axis direction LD from an inner peripheral edge (the left side of the valley of the substantially V-shaped crimp element 17 in FIG. 7). Thus, the two leg portions 17a are connected to the slit 21—free area of the extension portion 19a and to the end portion 19b of the bulge 19 through a linear portion extending substantially parallel to the axis direction LD. Incidentally, while the end portion 19b is preferably in a substantially semicircular shape, it may not be semicircular.

Each end portion of each coiled element 15 has a curved portion 15a. Each end portion of each coiled element 15 is connected through the curved portion 15a to each of the opposing top portions 17b (specifically the bulges 19 of them) of two adjacent rings 13. As shown in FIG. 6, the curved portion 15a of each end portion of the coiled element 15 has an arc shape. The coiled element 15 has a tangential direction at the connection end between the coiled element 15 and the top portion 17b of the ring 13 in the crimp pattern, and the tangential direction is coincident with the axis direction LD.

The transverse center of the end portion of the coiled element 15 is offset from (not coincident with) the peak (transverse center) of the top portion 17b of the ring 13. One transverse edge of the end portion of the coiled element 15 is coincident with a transverse edge of the top portion 17b of the ring 13.

The stent 11 with the structure described above not only has a high ability to conform to shape and to be radially compressed but also resists metal fatigue-induced breakage. In the stent 11, the bulge 19 provided in the top portion 17b of the crimp element 17 of the ring 13 is effective in reducing metal fatigue. In the stent 11, the slit 21 extending from an inner peripheral edge of the top portion 17b of the crimp element 17 of the ring 13 is effective in increasing the ability of the stent 11 to be radially compressed.

The conventional stent with a closed-cell structure is structurally less flexible and thus may buckle in a bent blood vessel to hinder blood flow. Moreover, if such a stent is locally deformed, the influence of its deformation will propagate not only in the radial direction RD of the stent but also in the axis direction LD of the stent, which makes it impossible for the stent to undergo local deformation independently. Due to this, such a stent may fail to conform to a complex vascular structure such as an aneurysm, so that a gap may occur between the circumferential wall of the stent and the vascular wall and that the stent may be more slidable in the vascular lumen as the blood vessel deforms in association with the pulsation, which may cause migration of the stent after placement.

In contrast, when the stent 11 according to this embodiment is deformed from an expanded state to a radially compressed state, the crimp pattern of the ring 13 is compressed so as to be folded and the coiled element 15 is tilted to the axis direction LD so as to be pulled in the axis direction LD like a coil spring. Considering one of the crimp elements 17 of the ring 13 in the crimp pattern in the stent 11, the crimp element 17 deforms as shown in FIG. 7, like opening and closing tweezers, when the stent 11 is radially compressed and expanded.

The stent 11 with the structure described above may be formed by laser-processing a tube including, for example, a biocompatible material, in particular preferably a tube made of a superelastic alloy. If the stent 11 should be made at a reduced cost from a superelastic alloy tube, the stent 11 is preferably formed by subjecting a superelastic alloy tube with a diameter of about 2 to 3 mm to laser processing and then expanding the tube to a desired diameter to subject the tube to shape-memory treatment. It will be understood that the stent 11 may be formed not only by laser processing but also by other methods such as cutting work.

In this regard, the outer diameter of the stent 11 is typically, but not limited to, 1.0 to 8.0 mm, and preferably 1.5 to 6.0 mm. The effective length of the stent 11 is typically 10 to 60 mm and preferably 40 to 60 mm. In general, if a stent has a high expansive force, such a stent should be designed to have a short effective length in view of the load on the vascular wall. On the other hand, the stent 11 according to this embodiment has a relatively low expansive force and thus can have a higher degree of freedom of effective length design.

The stent is preferably made of a highly rigid, biocompatible material. Such a material may be, for example, titanium, nickel, stainless steel, platinum, gold, silver, copper, iron, chromium, cobalt, aluminum, molybdenum, manganese, tantalum, tungsten, niobium, magnesium, calcium, or an alloy containing any of the above. Such a material may also be, for example, a synthetic resin material, such as a polyolefin such as polyethylene (PE) or polypropylene (PP), or polyamide, polyvinyl chloride, polyphenylene sulfide, polycarbonate, polyether, or polymethyl methacrylate. Such a material may also be, for example, a biodegradable resin (biodegradable polymer), such as polylactic acid (PLA), polyhydroxybutyrate (PHB), polyglycolic acid (PGA), or poly-ε-caprolactone.

Among these materials, titanium, nickel, stainless steel, platinum, gold, silver, copper, and magnesium or alloys containing any of them are preferred. Examples of such alloys include Ni—Ti alloys, Cu—Mn alloys, Cu—Cd alloys, Co—Cr alloys, Cu—Al—Mn alloys, Au—Cd—Ag alloys, and Ti—Al—V alloys. Examples of such alloys also include alloys of magnesium and Zr, Y, Ti, Ta, Nd, Nb, Zn, Ca, Al, Li, Mn, or the like. Among these alloys, Ni—Ti alloys are preferred.

Figure 10:
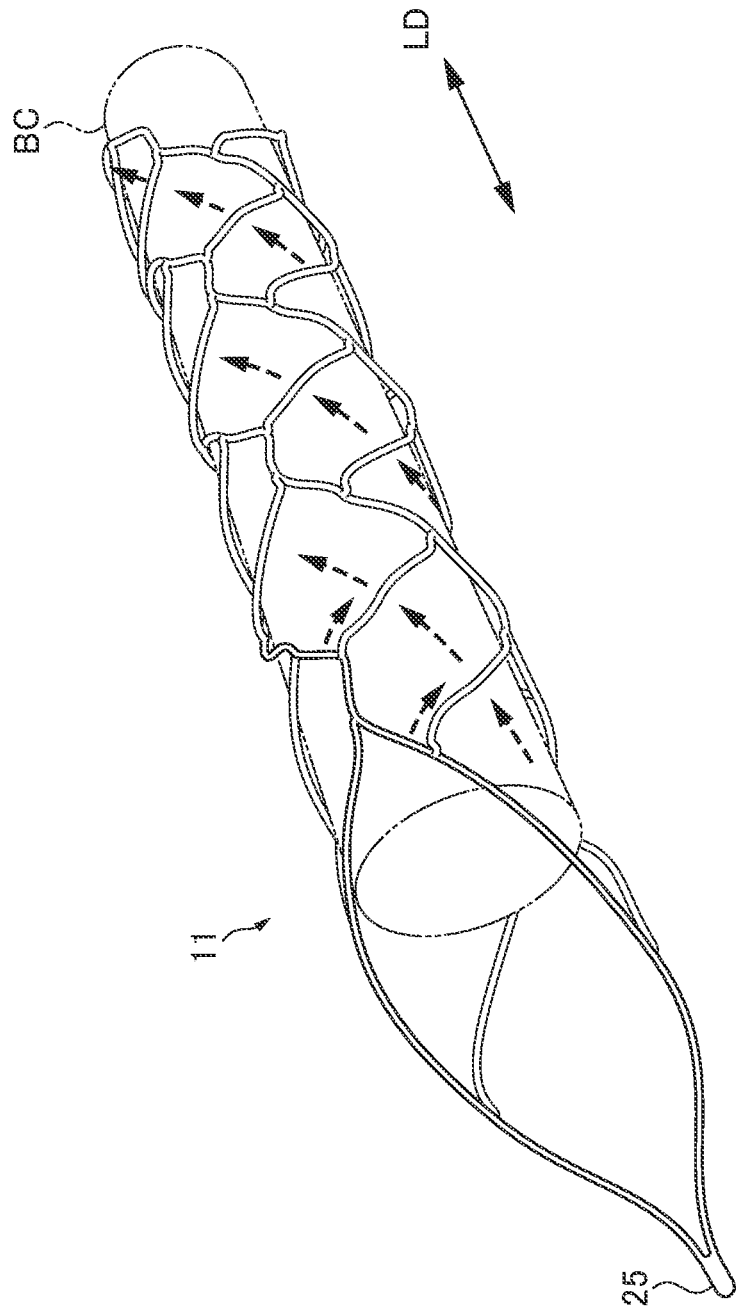
FIG. 10 is a view showing how the stent 11 captures a blood clot.

Next, an example of a method of using the catheter-stent system 10 equipped with the stent 11 will be described. FIGS. 8A to 8E are schematic views showing a procedure for removing a blood clot from a blood vessel using the catheter-stent system 10. In FIGS. 8A to 8E, solid lines are used to indicate the stent 11 and the wire 14 in the catheter 12 so that it can be easily understood how the stent 11 deploys. FIGS. 9A to 9D are schematic views showing how the stent 11 deploys and behaves when it is pushed out of the catheter 12. FIG. 10 is a schematic view showing how the stent 11 captures a blood clot.

Figure 8A:
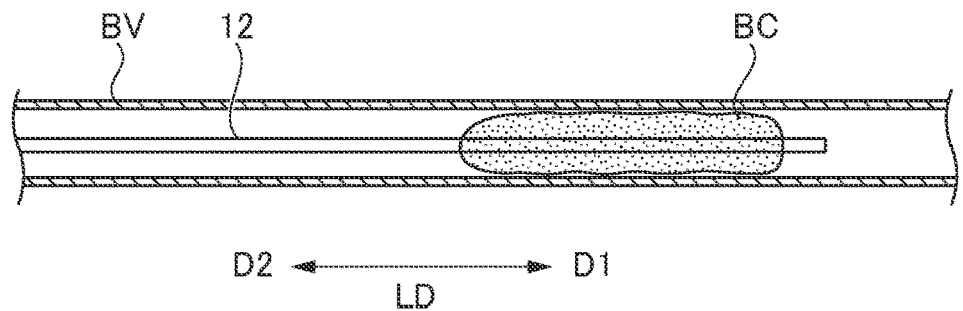
FIGS. 8A to 8E are schematic views showing a procedure for removing a blood clot from a blood vessel using the catheter-stent system 10.

First, as shown in FIG. 8A, the catheter 12 is inserted into a patient's blood vessel BV to reach the position of a blood clot BC at a lesion site. The catheter 12 is fed until its distal end reaches a side D1 distal to the blood clot BC. Subsequently, while being compressed radially, the stent 11 is inserted into the catheter 12. In the stent 11, the crimp pattern of the rings 13, the slit 21 in the top portion 17*b* of the ring 13, the curved portion 15*a* of the coiled element 15, and the tangent direction of the curved portion 15*a* (see FIGS. 3 to 5) coincident at the connection end with the axis direction LD work in a complex and synergetic manner to increase the ability to be compressed radially. Therefore, as compared to the conventional stent, the stent 11 can be easily inserted into a thinner catheter, so that the stent 11 can be used in a thinner blood vessel.

Figure 8B:
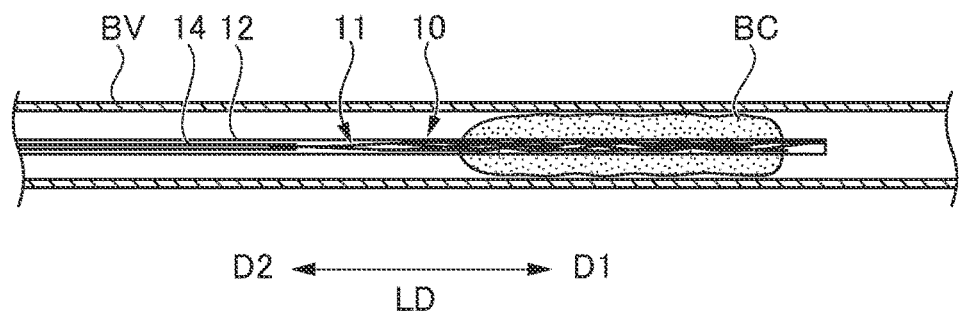

Subsequently, as shown in FIG. 8B, the wire 14 is manipulated to push the radially compressed stent 11 along the lumen of the catheter 12. The distal end of the stent 11 is then positioned at a side D1 distal to the blood clot BC. As mentioned above, the stent 11 according to this embodiment has a high ability to conform to shape. Therefore, even when the catheter 12 is inserted in a tortuous blood vessel BV, the stent 11 can be flexibly deformed along the catheter 12 and thus can be easily delivered to a lesion site such as a blood clot BC.

Figure 8C:
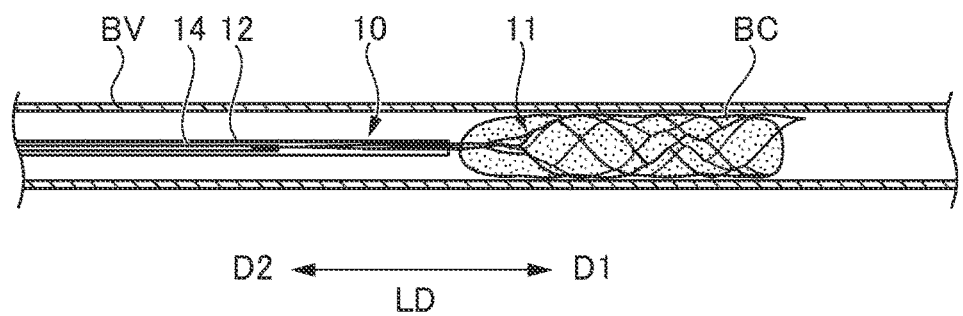
Figure 8D:
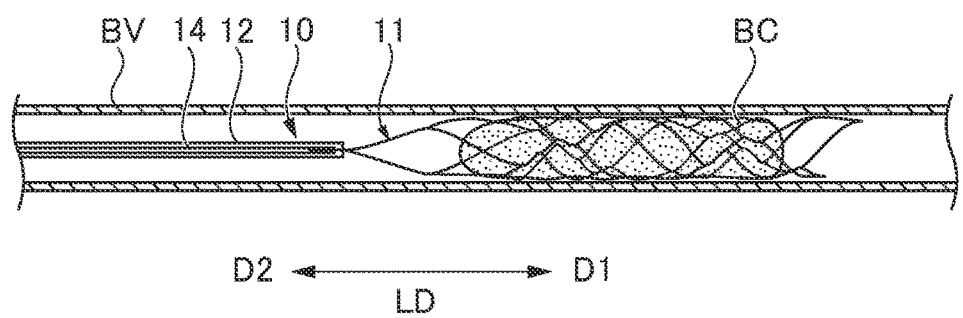
Figure 8E:
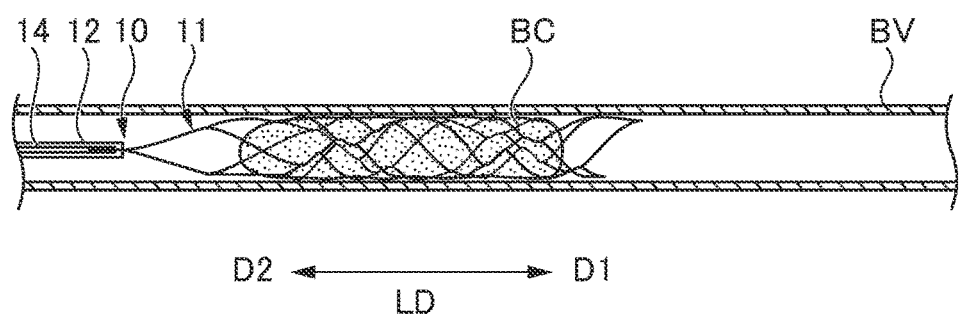
Figure 9A:
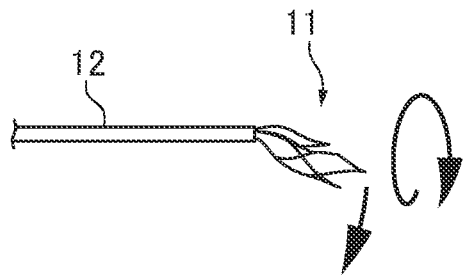
FIGS. 9A to 9D are schematic views showing how the stent 11 behaves when it is pushed out of a catheter 12 to deploy.
Figure 9B:
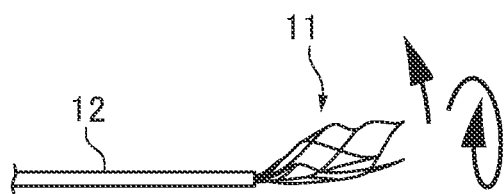
Figure 9C:
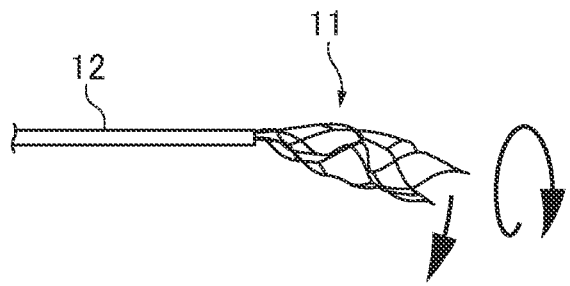
Figure 9D:
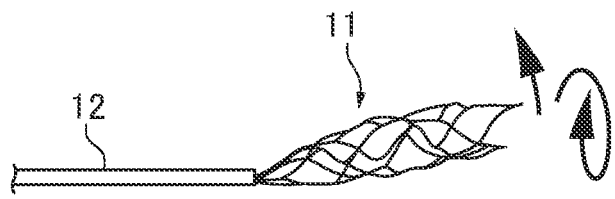

Subsequently, as shown in FIG. 8C, the stent 11 is pushed out of the distal end of the catheter 12 at the position of the blood clot BC and allowed to deploy. Specifically, the catheter 12 is pulled toward the proximal side D2 from the position shown in FIG. 8B so that the stent 11 is pushed out relative to the catheter 12. The stent 11 is entirely pushed out of the catheter 12. Moreover, the stent 11 being pushed out of the catheter 12 deploys while rotating and swinging as described later. This movement allows the deploying stent 11 to easily tangle with the captured blood clot BC. Subsequently, as shown in FIG. 8D, the wire 14 and the catheter 12 are pulled toward the proximal side D2. As a result, as shown in FIG. 8E, the stent 11, which captures the blood clot BC, is successfully pulled out of the body. According to the procedure using the catheter-stent system 10, the blood clot BC is successfully removed from the body.

Next, it will be described how the stent 11 behaves when it is pushed out of the catheter 12 to deploy. FIGS. 9A to 9D are schematic views showing how the stent 11 behaves when it is pushed out of the catheter 12 to deploy. FIG. 10 is a view showing how the stent 11 captures a blood clot. As described previously, the stent 11 is pushed out of the catheter 12 to deploy inside a blood vessel. Hereinafter, however, it will be described how the stent 11 behaves in an unrestrained state, which does not occur inside a blood vessel, when it is pushed out of the catheter 12 to deploy.

Since the stent 11 has the rings 13 and the coiled elements 15 configured as described above, the stent 11 deploys while rotating and swinging to one direction and another direction alternately as shown in FIGS. 9A to 9D when it is pushed out of the catheter 12. When the stent 11 capable of behaving in such a manner is pushed out of the catheter 12 to deploy inside a blood vessel, the stent 11 is actually not able to swing as shown above inside the blood vessel. Instead, as shown in FIG. 10, the stent 11 can easily tangle with the captured blood clot BC due to the action of the forces (indicated by the arrows in the drawing) that would allow the stent 11 to swing.

Also, as shown in FIG. 10, the struts tend to stretch in the axis direction LD while the stent 11 deploys. This improves the ability of the stent 11 to capture the blood clot BC (the ability of the stent 11 to easily tangle with the blood clot BC) and the ability of the stent 11 to conform to the shape of the blood vessel. Thus, the stent 11 according to this embodiment can be designed to have a smaller diameter over the entire length and can have high durability and high flexibility even when compressed radially.

Figure 11:
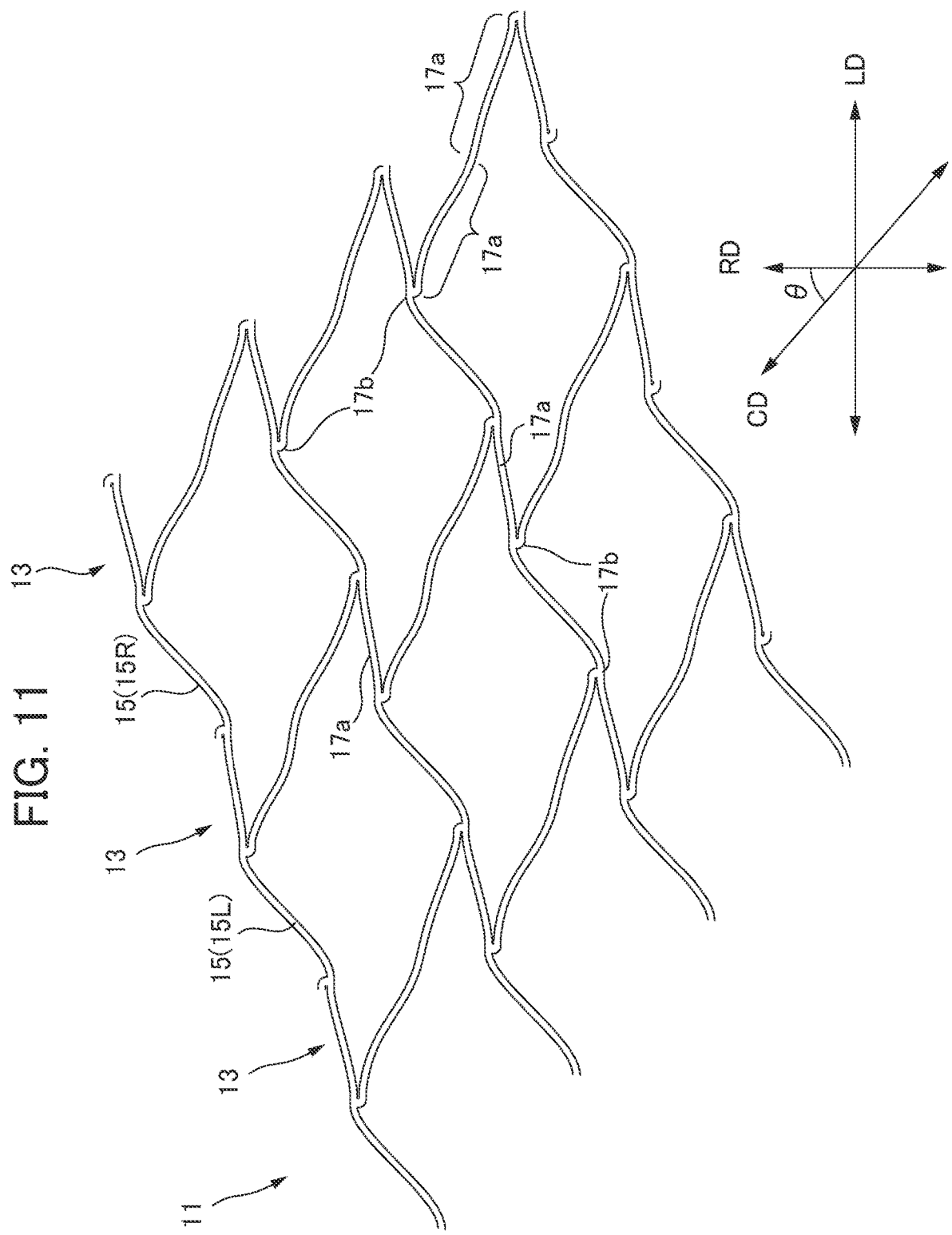
FIG. 11 is a perspective view of a stent 11 that is configured to swing only in one direction while rotating.

FIG. 11 is a perspective view of a stent 11 that is configured to swing only in one direction while rotating. As shown in FIG. 11, the stent 11 includes substantially parallelogrammatic cells arranged spirally and coiled elements 15R and 15L having the same winding direction so that it can behave so as to swing only in one direction while rotating. FIG. 11 shows an example in which the winding directions of the coiled elements 15R and 15L are both right-handed. Alternatively, they may be left-handed. It should be noted that the stent 11 may behave not only so as to swing continuously in one direction but also so as to swing intermittently in one direction or to alternately repeat rotation in one direction by a predetermined amount and subsequent rotation in the opposite direction by a predetermined amount.

FIG. 12 is a developed view of a stent 11 including cells with their physical properties partially modified so that the stent 11 is configured to swing while rotating. The stent 11 shown in FIG. 12 includes a plurality of cells of a uniform size, which are arranged to form a mesh, instead of the rings 13 and the coiled elements 15. FIG. 12 shows a state in which the substantially cylindrical stent 11 is developed in a plane. In FIG. 12, lines a, b, and c are drawn parallel to the rolling direction LR of the stent 11. When the stent 11 is rolled into a substantially cylindrical shape, the pair of points a1 and a2 on the line a, the pair of points b1 and b2 on the line b, and the pair of points c1 and c2 on the line c each provide a junction point in the rolling direction LR. It should be noted that FIG. 12 shows some of the junction points in the stent 11. In the stent 11 according to this embodiment, the junction points exist along the axis direction LD.

Cells CL1 hatched in FIG. 12 are adjusted to have a rigidity lower than that of other cells CL2 (blank). For example, only the cells CL2 may be plated with platinum, gold, or the like, while the cells CL1 may remain unplated, so that the cells CL1 have a rigidity lower than that of the cells CL2. In this case, the thickness of the plating layer may be adjusted to adjust the difference in rigidity between the cells CL1 and CL2. Alternatively, the stent 11 may include wire-shaped portions with the same line width made of a Ni—Ti alloy, in which only some of the wire-shaped portions, which form cells CL1, may have undergone ion implantation to have modified physical properties, so that the cells CL1 has a rigidity lower than that of other wire-shaped portions which form cells CL2.

The stent 11 shown in FIG. 12 may be rolled such that the pairs of points for junction, such as the pair of points a1 and a2 on the line a, the pair of points b1 and b2 on the line b, and the pair of points c1 and c2 on the line c, are joined along the axis direction LD to form a substantially cylindrical stent 11. In the developed state shown in FIG. 12, the stent 11 has a rolling direction LR inclined with respect to the direction LC in which the cells are aligned. This results in spiral arrangement of individual cells with respect to the axis direction LD in the substantially cylindrical stent 11. In the example shown in FIG. 12, the rolling direction LR of the stent 11 is inclined by an angle θc of about 15 degrees with respect to the direction LC in which the cells are aligned.

The stent 11 according to this embodiment is an example in which the physical properties of the cells are partially modified so that cells CL1 with a lower rigidity are arranged in at least one row in the rolling direction LR of the stent 11. In this regard, the cells CL1 with a lower rigidity are preferably not adjacent to each other in the rolling direction LR of the stent, and preferably, for example, the cells CL1 and CL2 are alternately arranged in the rolling direction LR of the stent. Such an arrangement makes the whole of the stent 11 more variable in physical properties. In the stent 11 according to this embodiment, the physical properties of the cell may include not only the rigidity of the cell but also parameters other than the rigidity of the cell. For example, the physical properties of the cell may include at least the elasticity of the cell, specifically, the Young's modulus or the like of the cell.

When the stent 11 according to this embodiment being radially compressed is inserted into the catheter 12, the cells CL1 with a relatively low rigidity tend to be more compressed by the pressure during the radial compression. Therefore, when the stent 11 is pushed out of the distal end of the catheter 12, the more compressed cells CL1 are arranged intermittently and spirally. As a result, the stent 11 deploys while rotating and swinging, when it is pushed out of the distal end of the catheter 12. Thus, the stent configured to deploy while rotating and swinging can tangle with a blood clot in a larger area and thus can have a higher ability to retrieve a blood clot as compared to a stent configured to deploy while rotating but substantially not swinging as shown in FIG. 13 described later. It should be noted that the stent 11 including the rings 13 and the coiled elements 15 as described above may also have the feature shown in FIG. 12, in which specific cells have a rigidity lower than that of other cells.

FIG. 13 is a developed view of a stent 11 that includes cells having different line widths, or the like so that the stent 11 is configured to rotate. The stent 11 shown in FIG. 13 includes a plurality of cells of a uniform size, which are arranged to form a mesh, instead of the rings 13 and the coiled elements 15. A cell row S1 hatched in FIG. 13 has a line width smaller than the line width of other cell rows S2. Thus, the cell row S1 has a rigidity lower than that of the cell rows S2. It should be noted that, in FIG. 13, which is a schematic view, the individual cell rows are illustrated to have the same line width.

The stent 11 as shown in FIG. 13 can be formed, for example, by laser-processing a metal tube to form a cell row S1 area with a line width of 50 μm and another cell row S2 area with a line width of 100 μm. Alternatively, the cell rows S1 and S2 may include wire-shaped portions with the same line width, and the cell rows S1 and S2 may have different line widths and different levels of rigidity depending on the presence and absence of a plating layer on the wire-shaped portion. For example, wire-shaped portions made of a Ni—Ti alloy may be plated with platinum, gold, or the like only in an area for forming the cell row S2 so that other areas forming the cell row S1 have a line width and a rigidity smaller than those of the cell row S2. In this case, the thickness of the plating layer may be adjusted to adjust the difference in line width and rigidity. Alternatively, the stent 11 may include wire-shaped portions with the same line width made of a Ni—Ti alloy, in which only some of the wire-shaped portions, which form the cell row S1, may have undergone ion implantation to have modified physical properties, so that other wire-shaped portions forming the cell row S1 have a line width and a rigidity smaller than those of the cell row S2.

When the stent 11 shown in FIG. 13 being radially compressed is inserted into the catheter 12, the cell row S1 with a relatively low rigidity tends to be more compressed by the pressure during the radial compression. Therefore, when the stent 11 is pushed out of the distal end of the catheter 12, the cell row S2 is obliquely inclined from the more compressed cell row S1 with respect to the axis direction LD. As a result, the stent 11 deploys while rotating along the direction in which the cell row is inclined, when it is pushed out of the distal end of the catheter 12. It should be noted that the stent 11 including the rings 13 and the coiled elements 15 as described above may also have the feature shown in FIG. 13, in which a specific cell row has a line width and a rigidity smaller than those of other cell rows.

Next, specific examples of the stent and the catheter-stent system according to the present invention will be described. As mentioned previously, the conventional stent has a relatively high expansive force so that it can have a high ability to capture a blood clot. However, if having too high an expansive force, such a stent may accidentally destroy a blood clot or increase the load on the vascular wall. If the expansive force of such a stent is reduced in order to avoid that, the resulting stent can be less capable of sufficiently expanding in the radial direction after it penetrates through a blood clot, so that the stent may fail to capture the blood clot when it is pulled. On the other hand, the stent 11 according to this embodiment can more easily tangle with a blood clot because it has a relatively low expansive force and is configured to deploy while rotating and swinging. Therefore, the stent 11 according this embodiment has an improved ability to capture a blood clot and thus provides a higher blood clot retrieval rate. The stent also has an improved ability to conform to the shape of a blood vessel.

The stent according to the present invention has an upper limit of expansive force of 0.05 N/mm and preferably 0.02 N/mm per unit length as measured under the conditions described below. The expansive force preferably has a lower limit of 0.001 N/mm and more preferably 0.01 N/mm. The stent having an expansive force per unit length in the above range can provide a higher blood clot retrieval rate and can prevent defects, such as accidental breakage of a blood clot and an increase in the load on the vascular wall. If a stent configured to deploy while rotating and swinging is designed to have a relatively high expansive force, it may cause friction with the vascular wall, and such friction may reduce the force for swinging. On the other hand, the stent 11 according to this embodiment has a relatively low expansive force, which prevents a reduction in the force for swinging due to friction with the vascular wall.

The stent preferably has a high level of smooth sliding property in a catheter. The sliding property of the stent is represented by the magnitude of the sliding resistance of the stent on surface. The magnitude of the sliding resistance can be expressed, for example, by the tensile load (N) applied when the stent is pulled in a single direction though a catheter. Regarding the sliding property (sliding resistance), which can be expressed by a tensile load, the stent according to the present invention may have an upper limit of tensile load of 3 N and preferably an upper limit of tensile load of 1 N as measured under the conditions described later. The tensile load may have a lower limit of 0.01 N and preferably 0.5 N. The stent having a tensile load in such a range has improved handleability for transfer through a catheter from outside the body to a lesion site or for transfer through a catheter from a lesion site to outside the body, and can more smoothly behave so as to deploy while rotating and swinging when going out of the distal end of a catheter.

Next, the results of testing on the expansive force and the sliding property of the stent according to the present invention will be described.

Expansive Force

Two stents having low expansive forces were prepared as Preparation Examples 1 and 2. A stent having a high expansive force was also provided as Conventional Example 1.

Conventional Example 1 is a general ready-made product used widely.

Tester used: Radial force testing system manufactured by Blockwise Engineering LLC Test Conditions:
 Temperature in the chamber of the tester: 37±2° C.
 Diameter of the stent for start of test: 0.5 mm (the stent is radially compressed inside a polymer tube in a catheter)
 Rate of increase of the diameter in the tester: 0.1 to 0.5 mm/s Test Method:
 (1) setting the temperature in the chamber of the tester at 37±2° C.;
 (2) placing the whole of the stent in the chamber of the tester and radially compressing the stent until the diameter for start of test is reached;
 (3) recording the expansive force in the radial direction while the diameter of the chamber in the tester is gradually increased at the rate of increase of the diameter; and
 (4) dividing the expansive force by the effective length of the stent to calculate the expansive force per unit length.

Figure 14A:
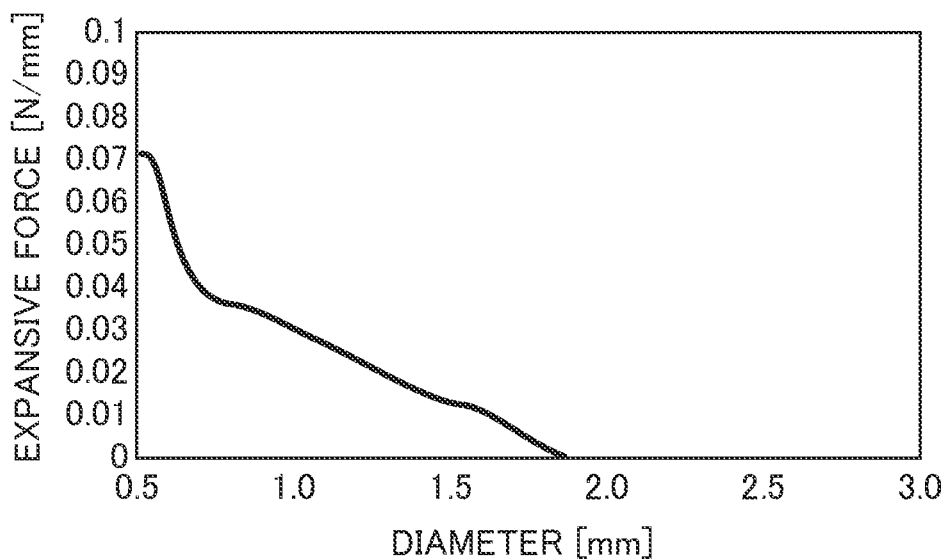
FIG. 14A is a graph showing how the expansive force changes as the stent of Preparation Example 1 is radially expanded.
Figure 14B:
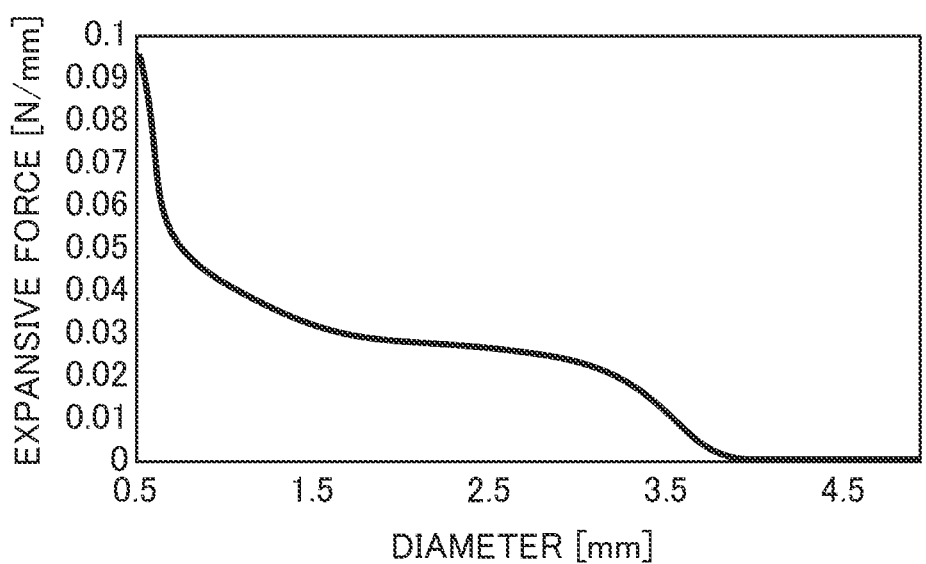
FIG. 14B is a graph showing how the expansive force changes as the stent of Preparation Example 2 is radially expanded.
Figure 15:
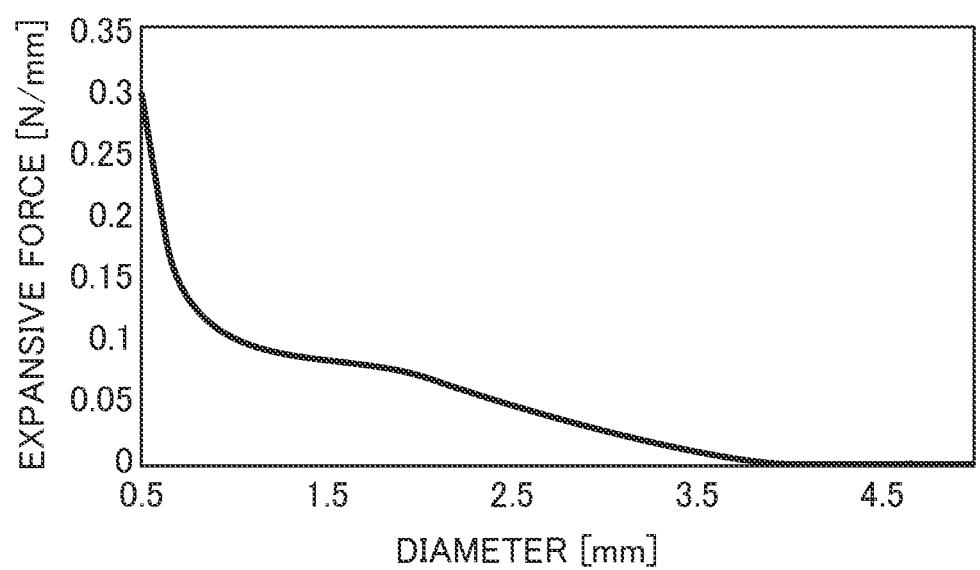
FIG. 15 is a graph showing how the expansive force changes as the stent of Conventional Example 1 is radially expanded.

FIGS. 14A, 14B, and 15 are graphs showing how the expansive force changes as the stents of Preparation Examples 1 and 2 and Conventional Example 1 are radially expanded under the measurement conditions above. The graphs of FIGS. 14A, 14B, and 15 show the relationship between the diameter (mm) of the radially expanded stent and the expansive force (N/mm) per unit length calculated for each diameter. FIG. 14A is a graph showing how the expansive force changes as the stent of Preparation Example 1 is radially expanded. FIG. 14B is a graph showing how the expansive force changes as the stent of Preparation Example 2 is radially expanded. FIG. 15 is a graph showing how the expansive force changes as the stent of Conventional Example 1 is radially expanded.

The stent of Preparation Example 1 is a type that has an outer diameter of 2 mm (tolerance: +0.2/−0.1) when it is radially expanded to the maximum. The stents of Preparation Example 2 and Conventional Example 1 are each a type that has an outer diameter of 4 mm (tolerance: +0.2/−0.1) when it is radially expanded to the maximum.

The expansive force of each of the stents of Preparation Examples 1 and 2 and Conventional Example 1 was measured with respect to the lower limit of the target blood vessel diameter. As a result, the following values were determined.
 Preparation Example 1: 0.015 (N/mm)
 Preparation Example 2: 0.026 (N/mm)
 Conventional Example 1: 0.074 (N/mm)

From the results of the test, the stents of Preparation Examples 1 and 2 were confirmed to satisfy the expansive force requirement for the stent according to the present invention (an expansive force of 0.05 N/mm or less per unit length). On the other hand, the stent of Conventional Example 1 was confirmed not to satisfy the expansive force requirement for the stent according to the present invention. As shown above, it can be verified using the above measurement conditions whether the subject stent satisfies the expansive force requirement for the stent according to the present invention.

Sliding Property

As a preparation example, a stent having a surface coating for reducing frictional resistance was prepared and then measured for tensile load under the conditions shown below. The stent of the preparation example is a type that has an outer diameter of 4 mm (tolerance: +0.2/−0.1) when it is radially expanded to the maximum, and satisfies the expansive force requirement for the stent according to the present invention (an expansive force of 0.05 N/mm or less per unit length).

Devices used: a microcatheter Headway 21 manufactured by MicroVention Inc.;
 a digital force gauge (push pull gauge);
 a pulling device;
 a thermostatic chamber; and
 a thermometer Test Conditions:
 Speed: 60 ram/min
 Pulling distance: the effective length+10 mm
 Test temperature: 37° C.±2° C.

Test Method:
 (1) confirming with the thermometer that the thermostatic chamber has a temperature of 37° C.±2° C.;
 (2) placing the microcatheter in the thermostatic chamber;
 (3) inserting a stent retriever into the microcatheter from the proximal side until the whole of the stent is housed in the microcatheter;
 in which the stent retriever is a device including the stent 11 according the embodiment and the wire 14 attached to the stent 11,
 (4) connecting the proximal end of the stent retriever to the digital force gauge disposed in the pulling device;
 (5) fixing the microcatheter with the stent retriever and the microcatheter arranged in a straight line and pulling the stent retriever constantly at the specified speed toward the proximal side using the pulling device; and
 (6) measuring tensile loads using the digital force gauge when the stent retriever is pulled over a distance equal to the effective length+10 mm and recording the minimum and maximum values of the tensile load. The test was repeated multiple times on the stent of the preparation example. As a result, the following values were obtained. Maximum value: 1.271 (N)

Minimum value: 0.706 (N)
Average: 1.007 (N)
Standard deviation: 0.207 (N)

From the test results, the stent of the preparation example was confirmed to satisfy the sliding property requirement for the stent according to the present invention (a tensile load of 3 N or less). As shown above, it can be verified using the above measurement conditions whether or not the subject stent satisfies the sliding property requirement for the stent according to the present invention.

Retrieval Rate Test

Next, a blood clot retrieval rate-measuring test using stents of examples and a comparative example and the results of the test will be described. The stents of Examples 1 to 4 and Comparative Example 1 subjected to the retrieval rate measurement each include the rings 13 and the coiled elements 15 and are each configured to swing while rotating (see FIG. 2). The stent of Example 5 includes a plurality of cells of a uniform size and is configured to swing while rotating. The stent of Example 5 includes cells CL1 and CL2 as shown in FIG. 12, in which the cells CL1 have a rigidity lower than that of the cells CL2. The stents of Examples 6 to 8 each include cells of a uniform size and are each configured to rotate. The stent of Example 6 includes cell rows S1 and S2 as shown in FIG. 13, in which the cell row S1 has a line width smaller than that of the cell rows S2. The stent of Example 7 includes cell rows S1 and S2 as shown in FIG. 13, in which the cell row S1 has no plating layer, whereas the cell rows S2 have a platinum plating layer. The stent of Example 8 includes cell rows S1 and S2 as shown in FIG. 13, in which only the cell row S1 has undergone ion implantation and thus has a rigidity lower than that of the cell rows S2, which have not undergone ion implantation.

A silicone tube with an inner diameter of 1.5 mm was provided as a model blood vessel for insertion of the stent of Example 1: 0.01 N/mm
Example 2: 0.03 N/mm
Example 3: 0.04 N/mm
Example 4: 0.05 N/mm
Example 5: 0.035 N/mm
Example 6: 0.04 N/mm
Example 7: 0.04 N/mm
Example 8: 0.05 N/mm
Comparative Example 1: 0.07 N/mm A retrieval test was carried out in which each of the above stents was used to retrieve the artificial blood clot from the model blood vessel. The retrieval process was according to the procedure shown in FIGS. 8A to 8E, which is described above. The retrieval of the artificial blood clot from the model blood vessel was attempted 60 times, and the retrieval rate was calculated as the ratio of the number of times of successful retrieval. A retrieval rate of less than 95.0% was evaluated as poor (x), 95.0% or more and less than 98.0% as fair (Δ), and 98.0% or more as good (○). Among them, the rates evaluated as poor (x) are not acceptable, whereas the rates evaluated as fair (Δ) and good (○) are acceptable. The term "fair" (Δ) means a rating level acceptable practically but slightly lower than the level "good" (○).

Table 1 shows the results of the evaluation of each of the stents of Examples 1 to 8 and Comparative Example 1 by the test.

TABLE 1

|  | Example 1 | Example 2 | Example 3 | Example 4 | Example 5 | Example 6 | Example 7 | Example 8 | Comparative Example 1 |
| --- | --- | --- | --- | --- | --- | --- | --- | --- | --- |
| Retrieval Rate (%) | 98.3 | 96.7 | 96.1 | 95.8 | 98.1 | 97.2 | 96.7 | 96.1 | 93.3 |
| Evaluations | ○ | Δ | Δ | Δ | ○ | Δ | Δ | Δ | × |

Example 1. Silicone tubes with an inner diameter of 2 mm were each provided as a model blood vessel for insertion of each of the stents of Examples 2 and 5 to 8 and Comparative Example 1. A silicone tube with an inner diameter of 1 mm was provided as a model blood vessel for insertion of the stent of Example 3. A silicone tube with an inner diameter of 3 mm was provided as a model blood vessel for insertion of the stent of Example 4. A sticky material of the same size, an imitation of a blood clot (hereinafter also referred to as the "artificial blood clot"), was placed in each of these silicone tubes. The artificial blood clot was prepared by softening clay with colored water.

The stents of Examples 1 to 8 are adjusted to have an expansive force of 0.05 N/mm or less per unit length. The stent of Comparative Example 1 is adjusted to have an expansive force more than 0.05 N/mm per unit length. The stent of Example 1 is a type that has an outer diameter of 2 mm (tolerance: ±0.2) when it is radially expanded to the maximum. The stents of Examples 2 and 5 to 8 and Comparative Example 1 are each a type that has an outer diameter of 4 mm (tolerance: ±0.2) when they are radially expanded to the maximum. The stent of Example 3 is a type that has an outer diameter of 1.5 mm (tolerance: ±0.2) when it is radially expanded to the maximum. The stent of Example 4 is a type that has an outer diameter of 6 mm (tolerance: ±0.2) when it is radially expanded to the maximum. The stents of Examples 1 to 8 and Comparative Example 1 had measured expansive forces per unit length as shown below when they each had a diameter equal to the lower limit of the diameter of the target blood vessel.

Table 1 indicates that the stent of Comparative Example 1 with an expansive force more than 0.05 N/mm per unit length yielded a retrieval rate of less than 95.0% and was evaluated as poor (x). On the other hand, among the stents of Examples 1 and 2 adjusted to have an expansive force of 0.05 N/mm or less per unit length, the stent of Example 2 yielded a retrieval rate of 96.7% and was evaluated as fair (Δ). The stent of Example 1 with an expansive force lower than that of Example 2 yielded a retrieval rate of 98.3% and was evaluated as good (○). The stent of Example 3 yielded a retrieval rate of 96.1% and was evaluated as fair (Δ). The stent of Example 4 yielded a retrieval rate of 95.8% and was evaluated as fair (Δ). The stent of Example 5 yielded a retrieval rate of 98.1% and was evaluated as good (○). The stents of Examples 6 to 8 yielded a retrieval rate of 95.2 to 96.1% and were all evaluated as fair (Δ).

These results demonstrate that the stents of Examples 1 to 8 can all yield a high blood clot retrieval rate. As compared to the stent of Comparative Example 1 with a high expansive force, the stents of Examples 1 to 8 would be less likely to break a blood blot into small pieces during the retrieval of the blood clot and less likely to fail to capture the blood clot and thus could retrieve a larger amount of the blood clot. The stent of Example 1 with the lowest expansive force, which yielded the highest retrieval rate, has been found to be able to yield a higher blood clot retrieval rate since it is configured to deploy while rotating and swinging. In particular, the rotation of the stent is good behavior for increasing the blood clot retrieval rate.

The stents of Examples 1 to 8 and Comparative Example 1 were each adjusted to have an effective length of 40 mm and then subjected to each of "evaluation of deflection of a model blood vessel" and "evaluation of degree of blood vessel damage in animal". The stents of Examples 1 to 8 and Comparative Example 1 were each adjusted to have the same expansive force as shown above. A test for evaluating model blood vessel deflection is carried out as follows. A bent model blood vessel (e.g., with a bending angle of 90 degrees) having an inner diameter equal to the target blood vessel diameter is provided, in which the stent is placed such that its center is located at the bending center, and a change in the angle of the bent portion of the model blood vessel is evaluated. The degree of blood vessel damage in an animal is evaluated as follows. In a laboratory animal, a blood vessel having the same diameter as the target blood vessel diameter is selected, and then the stent is allowed to deploy in the selected blood vessel and handled in the same way as for retrieval of a blood clot. Before and after the handling, imaging of the blood vessel is carried out for evaluation of blood vessel damage (e.g., bleeding). After several days (e.g., 30 days), angiography is carried out again, and the target blood vessel is pathologically investigated for any damage. The results of these evaluations show that the stents of Examples 1 to 8 are all evaluated as good for every item as compared to the stent of Comparative Example 1.

While stents according to embodiments of the present invention have been described, it will be understood that the embodiments are not intended to limit the present invention and may be altered or modified in various ways, such as those described below, and such modifications will also fall within the technical scope of the present disclosure.

(1) In the stent 11, one coiled element 15R may have the same length as that of another coiled element 15L. The lengths of one coiled element 15R and another coiled element 15L may both be larger or smaller than the length of the leg portion 17a. The spiral direction of the coiled elements 15 may be left-handed or right-handed. As a non-limiting example, the stent 11 includes the rings 13 and the coiled elements 15 in order to be configured to rotate. Alternatively, for example, the wire 14 may be rotated at the proximal side to rotate the stent 11.

(2) The stent 11 may have a structure in which a plurality of portions including struts (leg portions 17a) are missing. The stent 11 may include struts that are consecutive in the axis direction LD and thicker than other struts. In this case, the number of the consecutive thick struts may be two or more per stent.

(3) The stent 11 may further include a first additional strut that extends in the cyclic direction CD to link the adjacent coiled elements 15 in the cyclic direction CD. The stent 11 may further include a second additional strut that extends in a direction perpendicular to the cyclic direction CD to link the adjacent rings 13 in a direction perpendicular to the cyclic direction CD. A single piece of stent 11 may include both the first and second additional struts.

EXPLANATION OF REFERENCE NUMERALS

10: Catheter-stent system
11: Stent
12: Catheter
13: Ring (crimp pattern portion)
14: Wire
15: Coiled element
15L: Another coiled element
15R: One coiled element
17: Crimp element
17a: Leg portion
17b: Top portion
21: Slit
LD: Axis direction (central axis direction)
RD: Radial direction
CD: Cyclic direction

What is claimed is:

1. A stent configured to be inserted into a catheter and to be pushed out of the catheter to capture a blood clot in a blood vessel,
   the stent comprising a structure configured to deploy while rotating when a portion of the stent is pushed out of the catheter while another portion of the stent is inserted in the catheter,
   the stent having an expansive force of 0.05 N/mm or less per unit length when the stent has a diameter equal to a lower limit diameter of a target blood vessel and when the stent is measured
   using, as a tester, a radial force testing system manufactured by Blockwise Engineering LLC,
   using test conditions including
   a temperature of 37° C.±2° C. in a chamber of the tester,
   a stent diameter of 0.5 mm for start of test, and
   a rate of increase of diameter of 0.5 mm/s in the tester, and
   using a test method comprising:
   setting a temperature in the chamber of the tester at 37° C.±2° C.;
   placing whole of the stent in the chamber of the tester and radially contracting the stent until the stent has the diameter for the start of test;
   recording an expansive force in a radial direction while gradually increasing a diameter of the chamber at the rate of increase of diameter in the tester; and
   dividing the expansive force by an effective length of the stent to calculate an expansive force per unit length.

2. The stent according to claim 1, having a tensile load of 3 N or less as measured
   using a microcatheter Headway 21 manufactured by MicroVention Inc.,
   a digital force gauge or push pull gauge,
   a pulling device,
   a thermostatic chamber, and
   a thermometer,
   using test conditions including
   a speed of 60 mm/min,
   a pulling distance equal to the effective length+10 mm, and
   a test temperature of 37° C.±2° C., and
   using a test method comprising:
   confirming with the thermometer that the thermostatic chamber has a temperature of 37° C.±2° C.;
   placing the microcatheter in the thermostatic chamber;
   inserting a stent retriever into the microcatheter from a proximal side until whole of the stent is housed in the microcatheter;
   connecting a proximal end of the stent retriever to the digital force gauge disposed in the pulling device;
   fixing the microcatheter with the stent retriever and the microcatheter arranged in a straight line and pulling the stent retriever constantly at the specified speed toward the proximal side using the pulling device; and
   recording a maximum tensile load measured with the digital force gauge when the stent retriever is pulled over a distance equal to the effective length+10 mm.

3. The stent according to claim 1, wherein the structure is configured to deploy while rotating and swinging when a portion of the stent is pushed out of a catheter while another portion of the stent is inserted in the catheter.

4. The stent according to claim 3, comprising cells aligned in a direction, the stent having a rolling direction inclined with respect to the direction in which the cells are aligned,
   the stent including a plurality of cells arranged spirally around an axis direction, wherein the plurality of cells include at least one cell different in physical property from any other cell.

5. The stent according to claim 1, comprising a plurality of crimp pattern portions having a crimp pattern and arranged along an axis direction; and a plurality of coiled elements each provided between adjacent crimp pattern portions of the plurality of crim pattern portions and extending spirally around an axis, wherein
   each crimp pattern portion has a top portion, and each pair of opposite top portions of the adjacent crimp pattern portions are connected through each coiled element,
   each crimp pattern portion has a cyclic direction inclined with respect to a radial direction perpendicular to the axis direction when viewed in the radial direction, and one of the coiled elements at a one axial end of the crimp pattern portion has a winding direction the same as or opposite to that of another one of the coiled elements at another axial end of the crimp pattern portion.

6. A catheter-stent system comprising:
a catheter; and
the stent according to claim 1 that is configured to be inserted into the catheter and to be pushed out of the catheter.

* * * * *